United States Patent
Kopperschmidt et al.

(10) Patent No.: US 9,005,153 B2
(45) Date of Patent: Apr. 14, 2015

(54) METHOD AND APPARATUS FOR MONITORING A PERISTALTIC HOSE PUMP FOR CONDUCTING A FLUID IN A TUBING

(75) Inventors: Pascal Kopperschmidt, Dittelbrunn (DE); Reiner Spickermann, Wasserlosen-Burghausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 65 days.

(21) Appl. No.: 13/059,249

(22) PCT Filed: Aug. 14, 2009

(86) PCT No.: PCT/EP2009/005915
§ 371 (c)(1),
(2), (4) Date: May 18, 2011

(87) PCT Pub. No.: WO2010/020380
PCT Pub. Date: Feb. 25, 2010

(65) Prior Publication Data
US 2011/0230814 A1    Sep. 22, 2011

(30) Foreign Application Priority Data
Aug. 21, 2008  (DE) .......................... 10 2008 039 022

(51) Int. Cl.
*A61M 37/00* (2006.01)
*F04B 43/12* (2006.01)
(Continued)

(52) U.S. Cl.
CPC .................. *F04B 43/12* (2013.01); *A61M 1/16* (2013.01); *F04B 43/0081* (2013.01); *A61M 1/1037* (2013.01); *A61M 2205/3351* (2013.01);
(Continued)

(58) Field of Classification Search
USPC ........................................................ 604/6.11
See application file for complete search history.

(56) References Cited

U.S. PATENT DOCUMENTS 4,079,007 A * 3/1978 Hutchisson ...................... 210/85
4,083,777 A * 4/1978 Hutchisson ................... 210/646
(Continued)

FOREIGN PATENT DOCUMENTS

DE     19901078       2/2000
DE     10305036 A1    8/2004
(Continued)

OTHER PUBLICATIONS

International Search Report, PCT/EP2009/005915, mailed Jan. 19, 2010.
(Continued)

*Primary Examiner* — Tatyana Zalukaeva
*Assistant Examiner* — Guy K Townsend
(74) *Attorney, Agent, or Firm* — Kenyon & Kenyon LLP (57) ABSTRACT

The invention further relates to an apparatus and method for monitoring a peristaltic hose pump, in particular a peristaltic hose pump of an extracorporeal blood treatment device. The power consumed by the pump and/or the pressure in the tubing segment upstream or downstream of the pump is/are measured during operation of the pump and test signals $I_1(t)$, $I_2(t)$ which are associated with the individual displacement members are determined. The power or pressure signals associated with the individual displacement members significantly differ from each other during abnormal operation of the hose pump, but no significant differences can be recognized during normal operation of the pump.

15 Claims, 4 Drawing Sheets

(51) Int. Cl.
- *A61M 1/16* (2006.01)
- *F04B 43/00* (2006.01)
- *A61M 1/10* (2006.01)

(52) U.S. Cl.
CPC .. *A61M2205/3355* (2013.01); *A61M 2205/702* (2013.01); *F04B 2201/1203* (2013.01)

(56) References Cited

U.S. PATENT DOCUMENTS

| | | | | |
|---|---|---|---|---|
| 4,229,299 | A | * | 10/1980 | Savitz et al. .................... 210/85 |
| 4,732,765 | A | * | 3/1988 | Sasagawa et al. ............. 424/476 |
| 4,781,525 | A | | 11/1988 | Hubbard et al. |
| 4,828,543 | A | * | 5/1989 | Weiss et al. .................. 604/6.09 |
| 5,629,871 | A | | 5/1997 | Love et al. |
| 5,657,000 | A | * | 8/1997 | Ellingboe .................... 340/608 |
| 6,261,065 | B1 | | 7/2001 | Nayak et al. .................... 417/53 |
| 6,284,142 | B1 | * | 9/2001 | Muller ......................... 210/745 |
| 6,294,094 | B1 | * | 9/2001 | Muller et al. .................. 210/745 |
| 6,296,450 | B1 | | 10/2001 | Westberg et al. ................ 417/18 |
| 6,325,775 | B1 | * | 12/2001 | Thom et al. .................. 604/6.02 |
| 6,413,233 | B1 | * | 7/2002 | Sites et al. ................... 604/6.13 |
| 6,419,822 | B2 | * | 7/2002 | Muller ........................... 210/94 |
| 6,537,445 | B2 | * | 3/2003 | Muller ........................... 210/85 |
| 6,623,443 | B1 | | 9/2003 | Polaschegg |
| 6,716,004 | B2 | * | 4/2004 | Vandlik et al. ............. 417/477.2 |
| 6,723,062 | B1 | * | 4/2004 | Westberg et al. ........... 604/4.01 |
| 6,759,007 | B1 | * | 7/2004 | Westberg et al. ............... 422/44 |
| 8,043,076 | B2 | * | 10/2011 | Kopperschmidt ............ 417/476 |
| 2001/0021817 | A1 | | 9/2001 | Brugger et al. |
| 2003/0070969 | A1 | * | 4/2003 | Muller et al. ................... 210/91 |
| 2003/0130609 | A1 | * | 7/2003 | Nayak et al. ................. 604/6.11 |
| 2003/0138334 | A1 | * | 7/2003 | Vandlik et al. ............. 417/477.2 |
| 2004/0124157 | A1 | * | 7/2004 | Briggs et al. .................. 210/787 |
| 2004/0127840 | A1 | * | 7/2004 | Gara et al. ................... 604/4.01 |
| 2005/0049539 | A1 | * | 3/2005 | O'Hara et al. ............... 604/4.01 |
| 2005/0147529 | A1 | * | 7/2005 | Westberg et al. ............... 422/44 |
| 2005/0234384 | A1 | * | 10/2005 | Westberg et al. ............ 604/6.03 |
| 2005/0234385 | A1 | * | 10/2005 | Vandlik et al. .............. 604/6.03 |
| 2006/0032817 | A1 | * | 2/2006 | Westberg et al. ............. 210/645 |
| 2006/0042633 | A1 | * | 3/2006 | Bishop et al. .............. 128/207.18 |
| 2006/0106345 | A1 | * | 5/2006 | Flaker et al. .................. 604/131 |
| 2006/0155236 | A1 | * | 7/2006 | Gara et al. ................... 604/4.01 |
| 2006/0161092 | A1 | * | 7/2006 | Westberg et al. ............ 604/6.01 |
| 2006/0178611 | A9 | * | 8/2006 | Westberg et al. ............ 604/6.03 |
| 2006/0178612 | A9 | * | 8/2006 | Vandlik et al. .............. 604/6.03 |
| 2006/0186061 | A1 | * | 8/2006 | Briggs et al. .................. 210/787 |
| 2006/0189469 | A1 | * | 8/2006 | Briggs et al. .................... 494/23 |
| 2006/0205581 | A1 | * | 9/2006 | Chammas ....................... 494/16 |
| 2006/0217651 | A1 | * | 9/2006 | Hutchinson et al. ......... 604/6.01 |
| 2006/0219644 | A1 | * | 10/2006 | O'Hara et al. ................ 210/782 |
| 2006/0222561 | A1 | * | 10/2006 | Hutchinson et al. ........... 422/44 |
| 2006/0235348 | A1 | * | 10/2006 | Callicoat et al. ............. 604/4.01 |
| 2006/0293734 | A1 | * | 12/2006 | Scott et al. .................... 607/105 |
| 2007/0100272 | A1 | * | 5/2007 | Briggs ........................ 604/4.01 |
| 2008/0021377 | A1 | * | 1/2008 | Kienman et al. ............... 604/29 |
| 2008/0065007 | A1 | * | 3/2008 | Peterson et al. ................. 604/65 |
| 2008/0088820 | A1 | * | 4/2008 | Muller ........................... 356/39 |
| 2008/0094610 | A1 | * | 4/2008 | Muller ........................... 356/39 |
| 2009/0053083 | A1 | | 2/2009 | Kopperschmidt et al. |

FOREIGN PATENT DOCUMENTS

| | | |
|---|---|---|
| DE | 202007015453 U1 | 3/2008 |
| WO | 97/45150 A1 | 12/1997 |
| WO | 2007/104435 A2 | 9/2007 |
| WO | WO2007104435 * 9/2007 | ............. F04B 42/12 |

OTHER PUBLICATIONS

International Preliminary Report on Patentability for PCT/EP2009/005915 mailed on Mar. 3, 2011.

* cited by examiner

METHOD AND APPARATUS FOR MONITORING A PERISTALTIC HOSE PUMP FOR CONDUCTING A FLUID IN A TUBING

CROSS REFERENCE TO RELATED APPLICATIONS

This is a 371 national phase application of PCT/EP2009/005915 filed Aug. 14, 2009, claiming priority to German Patent Application No. 10 2008 039 022.4 filed Aug. 21, 2008.

FIELD OF INVENTION

The invention relates to a method of monitoring a peristaltic flexible tube pump for pumping a liquid in a flexible tubing line, and in particular a peristaltic flexible tube pump of an extra-corporeal blood-treating apparatus, which peristaltic flexible tube pump has a plurality of displacing bodies for occluding the flexible tubing line. As well as this, the invention also relates to an arrangement for monitoring a peristaltic flexible tube pump and in particular a peristaltic flexible tube pump of an extra-corporeal blood-treating apparatus, and to an extra-corporeal blood-treating apparatus having an arrangement for monitoring a peristaltic flexible tube pump.

BACKGROUND OF THE INVENTION

In an extra-corporeal blood treatment process, such as a hemodialysis for example, the blood to be treated flows, in an extra-corporeal blood circuit, through the blood chamber of a dialyser which is divided by a semi-permeable membrane into the blood chamber and a dialysis-fluid chamber, while dialysis fluid flows, in a dialysis-fluid system, through the dialysis-fluid chamber of the dialyser. The extra-corporeal blood circuit has an arterial flexible tubing line which runs to the blood chamber and a venous flexible tubing line which leads away from the blood chamber. The flexible tubing lines of the extra-corporeal blood-treating apparatus are generally provided in the form of disposable items intended to be used only once. The known pieces of blood-treating apparatus have a blood pump, which is generally arranged upstream of the blood chamber of the dialyser, to ensure that there is an adequate flow of blood in the extra-corporeal blood circuit.

There are stringent technical requirements which the blood pumps have to meet. There are therefore only certain types of pump which can be considered. What have proved successful in practice are flexible tube pumps which pump the patient's blood through the arterial and venous flexible tubing lines.

The flexible tube pumps are also referred to as peristaltic pumps from the way in which they operate. Their pumping action is based on the fact of at least one point of constriction or closure (an occlusion) moving along the elastic flexible tubing line which acts as a pumping chamber and thereby displacing the trapped liquid in the direction of pumping.

In the most widely used type of flexible tube pump, the setting is such that the elastic flexible tubing is completely closed off at the moving constrictions. These pumps are therefore also referred to as occlusive flexible tube pumps.

The movable constrictions or occlusions which carry the blood along in the flexible tubing in the pump may take different forms. Roller pumps are known in which the flexible tubing is inserted between a stator, which forms a curved roller track acting as an abutment, and a rotor which is mounted to be rotatable within the track and which is fitted with rollers, which means that the rollers roll over the flexible tubing in the direction of pumping. The rollers are preferably spring-mounted on the rotor so that they exert an applied compressive force on the flexible tubing. As well as the above, what are also known are finger pumps in which the occluding bodies are formed by a series of movable compressing members (fingers) arranged along the flexible tubing.

An overview of the different types of roller and finger pump is given in Dialysetechnik, 4th edition, Gesellschaft für angewandte Medizintechnik m.b.H. and Co. KG, Friedrichsdorf, 1988.

The requirements which exist for flexible tube pumps of this kind to operate properly in pieces of medical apparatus, and particularly in pieces of blood-treating apparatus, are demanding ones. In the known pieces of blood-treating apparatus, peristaltic flexible tube pumps are used not only to pump the blood but also to pump other liquids.

During the operation of the peristaltic flexible tube pump, there is a danger that the flexible tubing line inserted in the flexible tube pump may not be properly positioned in the bed of the pump or that the displacing bodies may not be guided properly over the flexible tubing line. If the peristaltic flexible tube pump has a fault of this kind, there is no guarantee that the pump will operate properly. If the segment of flexible tubing is not correctly positioned in the bed of the pump, there is a particular risk of the flexible tubing line being damaged. If nothing else, because of the possibility of the flexible tubing line not being adequately occluded there is no guarantee of the liquid being pumped properly.

U.S. Pat. No. 5,629,871 describes a method and an arrangement for monitoring the ability to operate of various sub-assemblies of a hemodialysis apparatus. These include the flexible tube pumps, with the current or the supply voltage to the flexible tube pumps being monitored to enable any failure of the pumps to be detected.

It is known from U.S. Pat. No. 4,781,525 for the current to a pump to be used to determine the pumping rate. WO 97/45150 describes a method of determining the pumping pressure of a pump in which the current to the pump is determined.

Known from WO 2007/104435 A2 is a method and an arrangement for operating an electric peristaltic flexible tube pump and in particular a flexible tube pump for pumping liquids in pieces of extra-corporeal blood-treating apparatus. To allow the proper operation of the flexible tube pump to be monitored, the power consumption of the pump, or a physical variable which correlates with its power consumption, is monitored. The monitoring of the current to the pump is based on the fact that the current to it has a D.C. component which does not vary cyclically and on which an A.C. component which does vary cyclically is superimposed. To allow the proper operation of the flexible tube pump to be monitored, the way in which the A.C. component of the power consumption rises and falls in relation to the D.C. component of the power consumption is monitored during the blood treatment.

SUMMARY OF THE INVENTION

One object underlying the invention is to monitor the proper operation of a peristaltic flexible tube pump which has a plurality of displacing bodies to occlude a flexible tubing line, and in particular a peristaltic flexible tube pump of an extra-corporeal blood-treating apparatus.

As well as this, another object underlying the invention is also to provide an arrangement for monitoring the proper operation of a peristaltic flexible tube pump, and in particular a peristaltic flexible tube pump of an extra-corporeal blood-treating apparatus.

A further object of the invention is to provide an extra-corporeal blood-treating apparatus having an arrangement for monitoring the proper operation of a peristaltic flexible tube pump.

The basis of the method according to the present invention and the arrangement according to the present invention is that, during the operation of the pump, the power consumed by the pump and/or the pressure in the segment of flexible tubing upstream or downstream of the pump is monitored, with the power and/or pressure being sensed in time ranges associated with respective ones of the displacing bodies so that measurement signals associated with the individual displacing bodies are obtained. The method according to the present invention and the arrangement according to the present invention are based on the finding that, if the flexible tube pump is not operating properly, the signals for power or pressure which can be associated with the individual displacing bodies differ from one another appreciably. When the pump is operating properly on the other hand, significant differences are not apparent in respect of power consumption or the pressure in the segment of flexible tubing upstream or downstream of the pump, because all the displacing bodies have the same effect on the power consumption or the pressure.

The power consumption and the pressure differ in a particularly significant way if the segment of flexible blood tubing is not properly positioned in the bed of the pump. However, improper guidance of the displacing bodies also results in asymmetries of this kind. In roller pumps for example, faults in the bearings of the rollers or in the return springs of the individual rollers may result in differences in respect of power consumption or pressure.

At the moment when the displacing bodies, such as the rollers of the roller pump, come to bear on the segment of the flexible tubing line, the power consumption of the pump increases, because the rollers begin to occlude the segment of the flexible tubing line at this moment. When on the other hand the rollers lift away again from the segment of the flexible tubing line, the power consumption of the pump goes down, because at this moment the rollers no longer have to occlude the segment of the flexible tubing line.

Provided the flexible tubing line is properly positioned in the bed of the pump and the displacing bodies occlude the flexible tubing line properly then, assuming the bearings of the rollers and the return springs are in proper order, no differences will be apparent in respect of power consumption and pressure when the individual rollers come to bear on the segment of the flexible tubing or move away from the segment of the flexible tubing. This will not be the case however if the flexible tubing line is not properly positioned in the bed of the pump or if bearings of rollers or return springs are faulty.

An indicator of improper operation of the pump is a difference which is of more than a preset size between the measurement signals which are associated with the individual displacing bodies, such as rollers of a roller pump for example. Means of the individual measurement signals over a preset interval of time may also be determined, to enable the means of the respective components to be compared with one another. This prevents interference signals superimposed on the measurement signals from being able to cause an incorrect assessment to be made. However, other statistical methods of assessment are, in principle, possible to enable differences between the signals to be found.

For the method according to the invention and the arrangement according to the invention, it is immaterial whether power consumption or pressure is measured directly or whether it is a variable which correlates with power consumption or pressure which is determined. The power consumption may for example be calculated from the product of the voltage applied to the electric motor of the blood pump multiplied by the current flowing into the motor. If however the voltage can be assumed to be constant, it is even enough for the current to be determined as a variable which correlates with power.

It is also immaterial how many displacing bodies the flexible tube pump has. Common types of roller pump have, as a rule, only two rollers. It would therefore be enough for one revolution of the roller pump through 360° to be divided into two time ranges each of 180°, which corresponds to half a revolution of the roller pump, to enable the two rollers each to be assigned an associated measurement signal.

The assignment of the associated individual measurement signals to the respective displacing bodies may be performed by dividing a full revolution into a number of angular ranges corresponding to the number of displacing bodies in the given case.

In a preferred embodiment of the invention, for the purpose of associating the measurement signals with the displacing bodies the positions of the individual displacing bodies are determined to enable it to be found whether the displacing body is situated in the given range. The finding of the positions of the displacing bodies can be performed in a simple and easy way by using the generally familiar Hall-effect sensors or by counting the revolutions of the pump while taking account of the number of displacing bodies.

In a further preferred embodiment of the invention, there is determined from the measurement signals which are associated with each of the individual displacing bodies a D.C. component and/or at least one A.C. component which is superimposed on the D.C. component, the D.C. components and/or the A.C. components of the measurement signals being compared with one another to enable a difference between the components in the individual measurement signals to be found which is significant of improper operation of the pump.

The determination of the D.C. and A.C. components of the measurement signals associated with the displacing bodies is preferably performed by a Fourier analysis.

The monitoring of the power consumption of a flexible tube pump of a blood-treating apparatus does not make it necessary for there to be any great cost or complication from the technical point of view. Nor does the monitoring of pressure involve any great technical cost or complication, because pressure sensors are generally present anyway in the extra-corporeal blood circuit of a blood-treating apparatus. The assessment of the measured variables for the purpose of determining whether the flexible tube pump is not operated properly can be carried out by the calculating and assessing unit (hardware and software) which is already present in known pieces of blood-treating apparatus to control and monitor the blood treatment. As a rule, all that is required for this purpose is appropriate programming. It is however also possible for the arrangement for monitoring the flexible tube pump to have a calculating and assessing unit of its own. The blood-treating apparatus and the monitoring arrangement may form a unitary piece of equipment or may also be different assemblies which can be operated independently of one another.

BRIEF DESCRIPTION OF THE DRAWINGS

Embodiments of the invention will be explained below by reference to the drawings.

In the drawings.

DETAILED DESCRIPTION OF THE DRAWINGS

Figure 1:
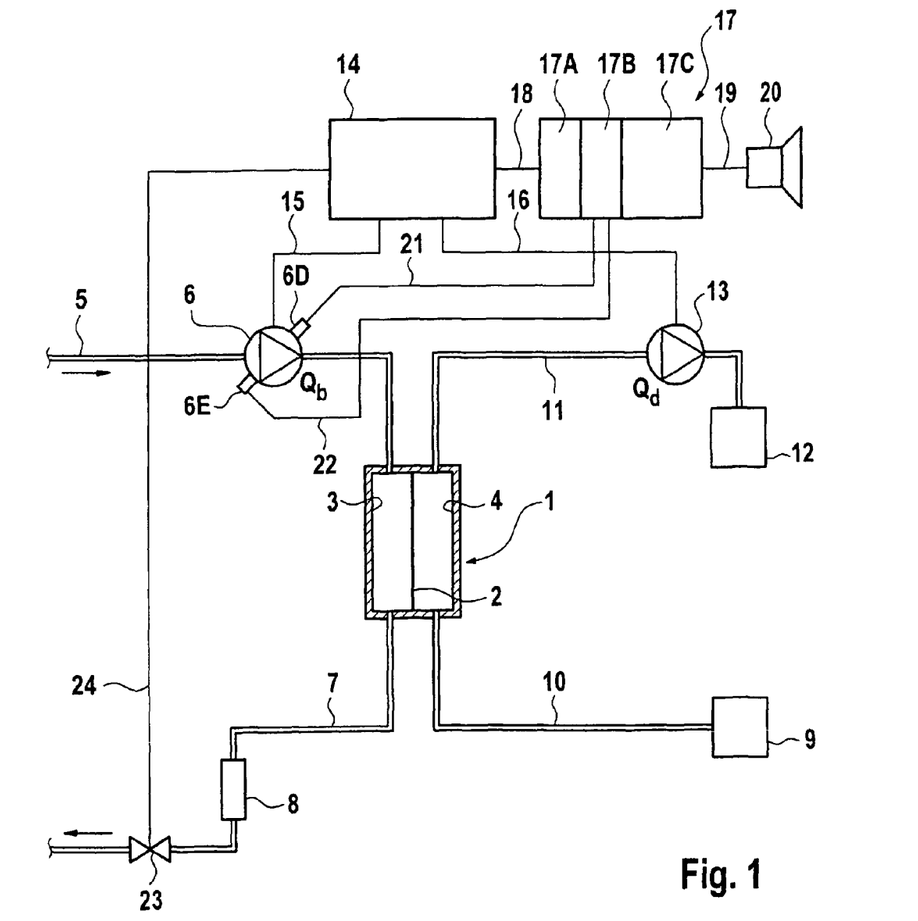
FIG. 1 is a simplified schematic view of an extra-corporeal blood-treating apparatus according to the invention which has an arrangement according to the invention for monitoring a peristaltic flexible tube pump of the blood-treating apparatus.

The extra-corporeal blood-treating apparatus, and in particular the hemodialysis apparatus, has a dialyser 1 which is divided by a semi-permeable membrane 2 into a blood chamber 3 and a dialysis-fluid chamber 4. From a patient, an arterial blood line 5 in which a blood pump 6 is inserted runs to an inlet of the blood chamber 3, whereas from an outlet of the blood chamber a venous blood line 7 runs, via a drip chamber 8, to the patient.

Fresh dialysis fluid is made available at a source 9 of dialysis fluid. From the source 9 of dialysis fluid, a dialysis-fluid infeed line 10 runs to an inlet of the dialysis-fluid chamber 4 of the dialyser 1, whereas a dialysis-fluid takeaway line 11 runs from an outlet of the dialysis-fluid chamber 4 to a discharge outlet 12. Inserted in the dialysis-fluid takeaway line 11 is a dialysis-fluid pump 13.

The blood pump 6 is an electrically operated peristaltic flexible tube pump, and in particular a roller pump, the arterial and venous blood lines 5, 7 being flexible tubing lines. The arterial flexible tubing line 5 is placed in the bed of the roller pump 6.

Figure 3:
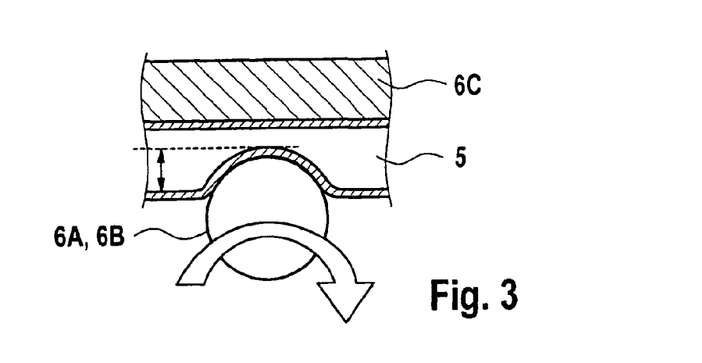
FIG. 3 shows the general arrangement of a roller pump.

Since roller pumps are generally familiar, there is no need for a detailed description. FIG. 3 is therefore only a general arrangement drawing showing the principle on which the roller pump 6 operates, which roller pump 6 has, in the present embodiment, two rollers 6A, 6B of which only one is shown in FIG. 3. The rollers 6A and 6B are rotatably mounted on a rotor (not shown). The flexible tubing line, which is the arterial blood line 5 in the present embodiment, is positioned between the rollers and a stator, which latter forms a roller track 6C acting as an abutment. The roller track 6C in which the arterial flexible tubing line 5 is positioned encloses the rotor fitted with rollers, the rollers being preloaded towards the roller track.

The dialysis apparatus has a central control unit 14 which is connected to the blood pump 6 and the dialysis-fluid pump 13 via control lines 15, 16. The control unit 14 supplies a given voltage and a given current to operate the blood pump 6 and the dialysis-fluid pump 13, and blood thus flows in the blood lines 5, 7 at a preset blood flowrate $Q_b$ and dialysis fluid thus flows in the dialysis-fluid lines 10, 11 at a preset dialysis-fluid flowrate $Q_d$.

The dialysis apparatus may also have other components such for example as a status-assessing means or ultrafiltration means and various sensors for monitoring the blood treatment but for the sake of greater clarity these have not been shown.

The arrangement according to the present invention for monitoring the proper operation of the flexible tube pump is described in the present embodiment in the form of part of the extra-corporeal blood-treating apparatus. In the present embodiment it is the blood pump 6 which is monitored. Basically however it is also possible for the proper operation of other pumps of the blood-treating apparatus to be monitored, such for example as that of a substituent pump.

Even though the arrangement for monitoring the blood pump is described in association with an extra-corporeal blood-treating apparatus in the present embodiment, the arrangement may however also be an independent sub-assembly which can be used, in all items of medico-technical equipment, for monitoring the proper operation of peristaltic flexible tube pumps.

The operation of the arrangement for monitoring the blood pump 6 will be described in detail in what follows.

The monitoring of the blood pump 6 is based, in the embodiment, on the assessment of the power consumed by the blood pump 6. The blood pump 6 has a D.C. electric motor to drive the rotor of the pump. Because the voltage which is applied in this case to the electric motor can be assumed to be constant, it is enough for the current flowing into the electric motor to be measured. It should be noted that in principle the blood pump may also be operated by an A.C. motor or other motorized drives.

The monitoring arrangement 17 has means 17A, which are only indicated diagrammatically, for determining the current to the pump I(t), which means 17A are connected, by a data line 18, to the central control unit 14 of the blood-treating apparatus, which central control unit 14 sets a given current to the pump 6 for the operation of the said pump.

The monitoring arrangement 17 also has means 17B for sensing the current to the pump $I_{1,2}(t)$ which is associated with the first or second displacing body, such for example as with the first or second roller 6A or 6B of the roller pump 6. The current to the pump $I_{1,2}(t)$ for the first or second roller 6A, 6B produces a first or second measurement signal, which signals can be compared with one another. For this purpose, the monitoring arrangement 17 has means 17C for comparing the measurement signals $I_1(t)$ and $I_2(t)$ associated with the two rollers 6A and 6B. On the basis of the comparison of the two measurement signals it is concluded that the pump is operating properly or is not operating properly.

If the pump is not operating properly, a control signal is generated which is transmitted via the data line 18 to the central control unit 14 of the blood-treating apparatus. The central control unit 14 of the blood-treating apparatus can then take action on the system controlling the machinery. Also, if the pump is found not to be operating properly, an alarm signal can be generated which is transmitted via a data line 19 to a visual and/or audio alarm unit 20 which gives a visual and/or audio alarm.

Figure 4A:
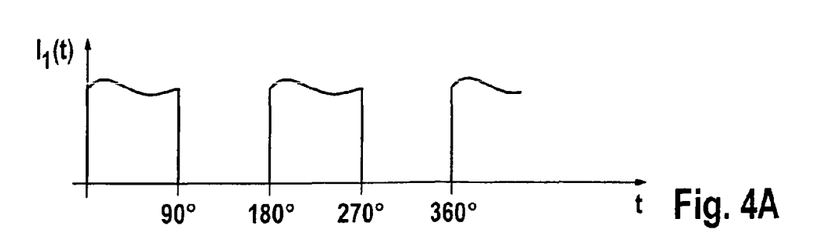
FIG. 4A shows the measurement signal which is associated with the first displacing body of the flexible tube pump, when the flexible tube pump is operating properly.
Figure 4B:
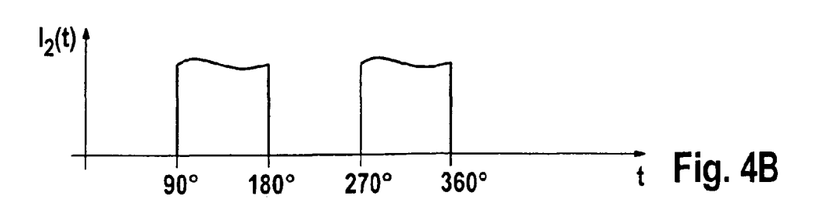
FIG. 4B shows the measurement signal which is associated with the second displacing body, when the flexible tube pump is operating properly.
Figure 5A:
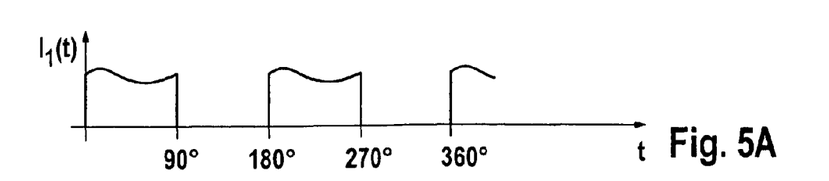
FIG. 5A shows the measurement signal which is associated with the first displacing body of the flexible tube pump, when the flexible tube pump is not operating properly.
Figure 5B:
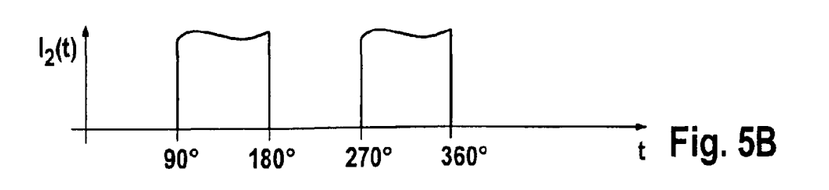
FIG. 5B shows the measurement signal which is associated with the second displacing body, when is not operating properly.
Figure 6A:
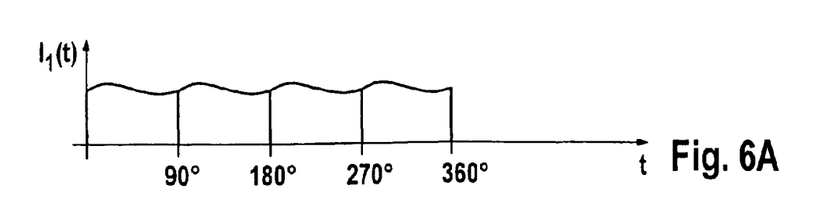
FIG. 6A shows the first measurement signal, for the first displacing body, before it is broken down into a D.C. component and one or more A.C. components (harmonics) by means of a Fourier analysis, when the flexible tube pump is not operating properly.
Figure 6B:
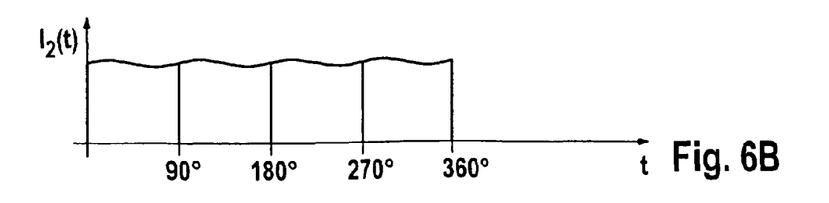
FIG. 6B shows the second measurement signal, for the second displacing body, before it is broken down into D.C. and A.C. components, when the flexible tube pump is not operating properly.

Referring to FIGS. 4 to 6, the assignment of the associated measurement signals to the two displacing bodies 6A and 6B of the peristaltic flexible tube pump will be described in what follows.

A revolution of the rotor of the roller pump 6 carrying the rollers 6A and 6B is divided into a first angular range of 0-180° and a second angular range of 180-360°. The first angular range of 0-180° is assigned to be associated with the first roller 6A while the second angular range of 180-360° is assigned to be associated with the second roller 6B. To enable the positions of the rollers 6A and 6B to be found, the roller pump 6 has first and second Hall-effect sensors 6D and 6E which are assigned to respective ones of the two angular ranges. It is also possible for only one Hall-effect sensor to be used and for the angular ranges lying between two signals from the sensor to be interpolated over the elapsed time. When the first roller 6A enters the first angular range, the first Hall-effect sensor 6D generates a signal, whereas the second Hall-effect sensor 6E generates a signal when the second roller 6B enters the second angular range. The signals from the Hall-effect sensors need not strictly correspond geometrically to the position of a roller. Instead the association may equally well be made by using an appropriate offset angle. The two signals are received by the means 17B for sensing the currents associated with the rollers via data lines 21, 22. The means 17B for sensing the respective currents to the pump generate a first signal $I_1(t)$ which corresponds to the current to the pump measured in the first angular range 0-180° and a second measurement signal $I_2(t)$ which corresponds to the current measured in the second angular range of 180-360°.

FIG. 4A shows the pump current $I_1(t)$ associated with the first roller 6A, whereas FIG. 4B shows the pump current $I_2(t)$ associated with the second roller 6B. FIGS. 4A and 4B show the case where the blood pump is operating properly. In this case the currents to the pump $I_1(t)$ and $I_2(t)$ associated with the two rollers are not substantially different from one another, i.e. slight differences can, at most, be seen.

FIGS. 5A and 5B on the other hand show the case where the blood pump is not operating properly. In this case the current to the pump $I_1(t)$ which is associated with the first roller differs from the current to the pump $I_2(t)$ which is associated with the second roller. The first current to the pump is smaller than the second current to the pump. When this is the case, the flexible tubing line may for example not be inserted properly in the abutment for the rollers or the bearing or the return spring of one of the two rollers may be faulty. The state of improper operation is established by comparing the two pump currents $I_1(t)$ and $I_2(t)$.

For the comparison of the currents to the pump, the arrangement according to the invention makes provision for a Fourier analysis of the current to the pump. For this purpose, respective continuous measurement signals $I_1(t)$ and $I_2(t)$, which are shown in FIGS. 6A and 6B, are generated from the first measurement signal WO, which covers only the first angular window, and from the second measurement signal $I_2(t)$ which covers only the second angular window. For this purpose, the current to the pump for the preceding or succeeding angular range may for example be taken for whichever angular range is not sensed in the given case. The first measurement signal $I_1(t)$ is for example obtained by taking the measurement signal for the preceding angular range of 0-180° each time for the second angular range of 180-360°. The measurement signal $I_2(t)$ which is associated with the second roller is generated in a corresponding way. The person skilled in the art will also be familiar with other mathematical methods to enable the two measurement signals to be assessed by a Fourier analysis.

The two measurement signals $I_1(t)$ and $I_2(t)$ are then broken down into a D.C. component and the first harmonic by a Fourier analysis. The measurement signal may however also be broken down into other harmonics which are taken as a basis for the assessment. For this purpose, the means 17C for comparing the currents to the pump have means for making a Fourier analysis.

Figure 7:
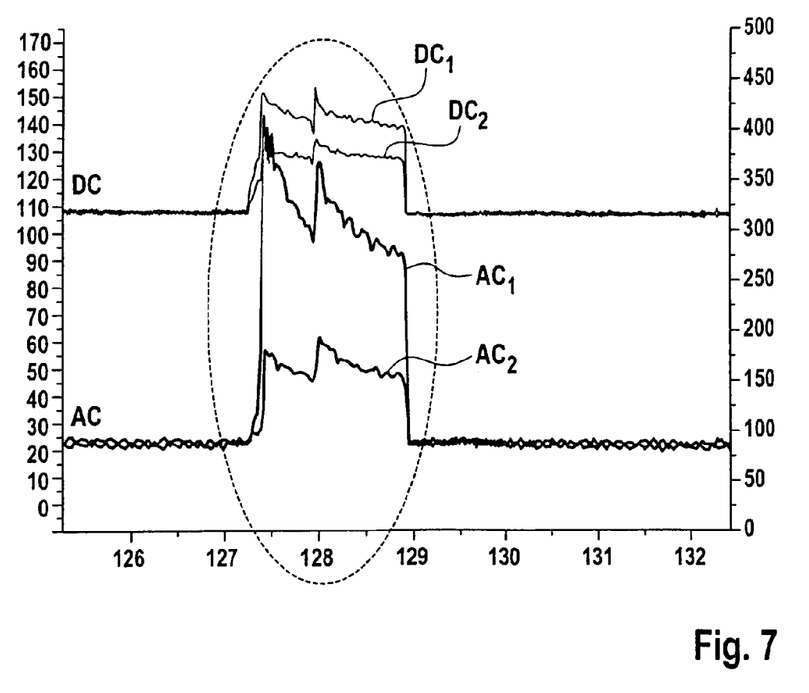
FIG. 7 shows the D.C. and A.C. components (harmonics) of the measurement signals associated with the two displacing bodies after a breakdown.

FIG. 7 shows the result of the Fourier analysis of the two currents to the pump. During proper operation of the blood pump (which is not the case shown in FIG. 7), the D.C. components $DC_1$ and $DC_2$ do not differ from one another. Nor do the first harmonics $AC_1$ and $AC_2$ differ substantially from one another while the pump is operating properly. In the event of improper operation by the pump on the other hand, which is the case shown in FIG. 7, D.C. component $DC_1$ differs appreciably from D.C. component $DC_2$. The first harmonic $AC_1$ too differs appreciably from the second harmonic $AC_2$. To establish that the pump is not operating properly, the means 17C for comparing the currents to the pump either compare the D.C. component $DC_1$ which is associated with the first roller of the roller pump with the D.C. component $DC_2$ which is associated with its second roller, and/or compare the first harmonic $AC_1$ for the first roller with the first harmonic $AC_2$ for the second roller.

If the difference between the two A.C. components $AC_1$ and $AC_2$ and/or between the two D.C. components $DC_1$ and $DC_2$ is of more than a preset size, it is concluded that the pump is not operating properly, which is the case if, for example, the segment of flexible blood tubing is not properly positioned in the bed of the pump or if the return spring of one of the two rollers is faulty. In the present embodiment, improper operation of the blood pump becomes apparent on the time scale at between approximately 127 and 129 minutes. It having been found that the blood pump is not operating properly, the control signal for the control unit 14 and the alarm signal for the alarm unit 20 are generated, which means that action is taken in the control system of the machinery and an alarm is given. The action taken in the control system of the machinery may for example be that the blood pump 6 is stopped and a tube clamp 23 arranged on the venous blood line 7 is closed, which tube clamp 23 is connected to the control unit 14 by a control line 24.

Figure 2:
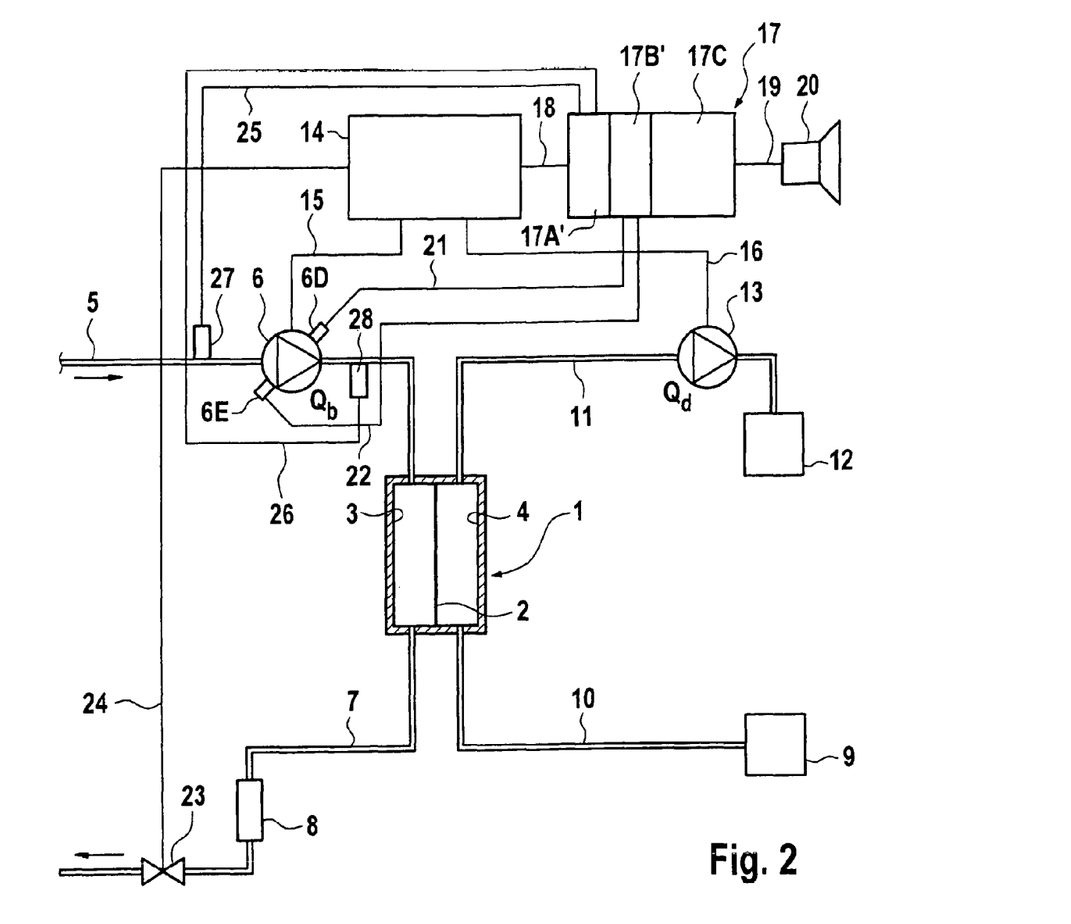
FIG. 2 shows an alternative embodiment of the extra-corporeal blood-treating apparatus according to the invention having the arrangement according to the invention for monitoring the flexible tube pump.

FIG. 2 shows an alternative embodiment of the invention which differs from the embodiment which has been described by reference to FIG. 1 only in that the assessment is made not on the basis of power consumption but on the basis of the pressure in the arterial blood line upstream or downstream of the blood pump 6. Those parts of the blood-treating apparatus and the monitoring arrangement which correspond to one another are therefore given the same reference numerals. Instead of the means (17A) for determining the current to the pump, the monitoring arrangement 17 has means 17A' for determining the pressure in the arterial blood line 5 upstream and downstream of the blood pump 6, which means 17A' are connected, via data lines 25 and 26 respectively, to a pressure sensor 27 upstream of the blood pump 6 and a pressure sensor 28 downstream of the pump. Instead of the means (17B) for sensing the currents to the pump associated with the individual displacing bodies, means (17B) for sensing the pressures associated with the displacing bodies are provided. Although there are the two pressure sensors shown in FIG. 2, a pressure measurement upstream or downstream of the blood pump 6 is, in principle, enough.

The assessment of the measurement signals takes place in the same way in the alternative embodiment as in the first embodiment which makes provision for an assessment of the power consumption of the blood pump. The only difference is that instead of the current to the pump it is pressure which is measured and which is associated with the individual displacing bodies. Reference should therefore be made to the description of FIG. 1.

The invention claimed is:

1. A method of monitoring a peristaltic flexible tube pump for pumping a liquid in a flexible tubing line, the peristaltic flexible tube pump having a at least first and second individual displacing bodies for occluding the flexible tubing line, said method comprising:
   operating the pump;
   determining a power consumed by the pump, or a variable which correlates with this power, or a pressure in a segment of the flexible tubing line upstream or downstream of the pump, or a variable which correlates with this pressure during the operation of the pump, using a power or pressure sensor sensing a measurement signal corresponding to the power or pressure of the pump;
   sensing the power consumed by the pump, the variable which correlates with this power, the pressure in the segment of the flexible tubing line upstream or downstream of the pump, or the variable which correlates with this pressure for time ranges associated with respective ones of the individual displacing bodies, the sensing using a power or pressure sensor sensing a measurement signal corresponding to the power or pressure of the pump;
   comparing a first measurement signal associated with the first individual displacing body with a second measurement signal associated with the second individual displacing body to determine a difference between the measurement signals of the first and second individual displacing bodies; and
   electronically indicating that the pump is not operating properly if the difference between the measurement signals of the first and second individual displacing bodies is larger than a preset size.

2. The method according to claim 1, further comprising:
   determining a D.C. component or at least one A.C. component that is superimposed on the D.C. component from the measurement signals associated with each of the individual displacing bodies; and
   comparing the D.C. component or the A.C. component of the measurement signals associated with the first individual displacing body with the D.C. component or the A.C. component of the measurement signals associated with the second individual displacing body.

3. The method according to claim 2, further comprising:
   determining a mean of the D.C. component or the A.C. component associated with each of the individual displacing bodies in a preset interval of time; and
   comparing the mean of the D.C. component or the A.C. component associated with the first individual displacing body with the mean of the D.C. component or the A.C. component associated with the second individual displacing body; and
   electronically indicating that the flexible tube pump is not operating properly if a difference between the means of the first and second individual displacing bodies is larger than a preset size.

4. The method according to claim 2, further comprising: performing a Fourier analysis to determine the D.C. or A.C. components of the measurement signals.

5. The method according to claim 1, further comprising:
   determining a position of the first and second individual displacing bodies for the purpose of associating the measurement signals with each of the first and second individual displacing bodies.

6. The method according to claim 1, wherein the flexible tube pump is an occlusive roller pump, and the flexible tubing line is arranged between a stator which forms a roller track acting as an abutment and a rotor fitted with rotatably mounted rollers.

7. The method according to claim 1, wherein the peristaltic flexible tube pump is part of an extra-corporeal blood-treating apparatus.

8. The method according to claim 7, wherein said extra-corporeal blood treating apparatus comprises a blood-treating unit, an arterial flexible tubing line running to the blood-treating unit, and a venous flexible tubing line leading away from the blood-treating unit, and the peristaltic flexible tube pump is arranged in the arterial flexible tubing line.

9. An arrangement for monitoring a peristaltic flexible tube pump for pumping a liquid in a flexible tubing line, the flexible tube pump having a plurality of individual displacing bodies for occluding the flexible tubing line, the arrangement comprising:
   a sensor configured to detect a value of a power consumed by the pump during operation of the pump or a variable which correlates with this power, or a pressure in a segment of the flexible tubing line upstream or downstream of the pump or a variable which correlates with this pressure, wherein the sensor is configured such that measurement signals associated with each of the individual displacing bodies are determined for time ranges associated with respective ones of the individual displacing bodies; and
   a device configured to compare a change in the pump power or pressure by comparing a first measurement signal associated with a first individual displacing body with a second measurement signal associated with a second individual displacing body configured such that an electronic indication is provided when the flexible tube pump is not operating properly if a difference between the measurement signals of the first and second individual displacing bodies is larger than a preset size.

10. The arrangement according to claim 9, wherein the device configured to compare the change in the pump power or pressure by comparing the measurement signals is configured such that there is determined from the measurement signals associated with each of the individual displacing bodies a D.C. component, or at least one A.C. component which is superimposed on the D.C. component, the D.C. component or the A.C. component of the measurement signals associated with the first individual displacing body being compared with the D.C. component or the A.C. component of the measurement signals associated with the second individual displacing body.

11. The arrangement according to claim 9, wherein the device configured to compare the change in the pump power or pressure by comparing the measurement signals comprises a device configured to perform a Fourier analysis to determine the D.C. or A.C. components of the measurement signals.

12. The arrangement according to claim 9, wherein the flexible tube pump is an occlusive roller pump, and the flexible tubing line is arranged between a stator which forms a roller track acting as an abutment and a rotor fitted with rotatably mounted rollers.

13. The arrangement according to claim 9, wherein the sensor configured to detect the value of the power consumed by the pump or the pressure comprises a device configured to determine a position of each of the individual displacing bodies for the purpose of associating the measurement signals with each of the individual displacing bodies.

14. The arrangement according to claim 9, wherein the peristaltic flexible tube pump is part of an extra-corporeal blood-treating apparatus.

15. A blood-treating apparatus comprising:
- a blood-treating unit;
- an arterial flexible tubing line running to the blood-treating unit;
- a venous flexible tubing line leading away from the blood-treating unit;
- a peristaltic flexible tube pump arranged in the arterial flexible tubing line; and
- the arrangement according to claim 9.

\* \* \* \* \*